US008921592B2

(12) United States Patent
Yang et al.

(10) Patent No.: US 8,921,592 B2
(45) Date of Patent: Dec. 30, 2014

(54) PROCESS OF PRODUCING OXALATE BY CO GAS PHASE METHOD

(75) Inventors: Weimin Yang, Shanghai (CN); Juntao Liu, Shanghai (CN); Wanmin Wang, Shanghai (CN); Lei Li, Shanghai (CN)

(73) Assignees: China Petroleum & Chemical Corporation, Beijing (CN); Shanghai Research Institute of Petrochemical Technology, SINOPEC, Shanghai (CN)

( * ) Notice: Subject to any disclaimer, the term of this patent is extended or adjusted under 35 U.S.C. 154(b) by 2 days.

(21) Appl. No.: 13/702,280

(22) PCT Filed: Jun. 9, 2011

(86) PCT No.: PCT/CN2011/000965
§ 371 (c)(1),
(2), (4) Date: Dec. 5, 2012

(87) PCT Pub. No.: WO2011/153825
PCT Pub. Date: Dec. 15, 2011

(65) Prior Publication Data
US 2013/0079549 A1 Mar. 28, 2013

(30) Foreign Application Priority Data
Jun. 11, 2010 (CN) .......................... 2010 1 0200028

(51) Int. Cl.
C07C 69/36 (2006.01)
C07C 67/36 (2006.01)
B01J 23/44 (2006.01)

(52) U.S. Cl.
CPC . *C07C 67/36* (2013.01); *B01J 23/44* (2013.01)
USPC ......................................... 560/204; 560/190

(58) Field of Classification Search
USPC ................................. 560/204, 190
See application file for complete search history.

(56) References Cited

U.S. PATENT DOCUMENTS

| 4,203,959 A | 5/1980 | Munster |
| 4,461,909 A | 7/1984 | Tahara et al. |
| 4,908,466 A | 3/1990 | Nelson |
| 5,054,317 A | 10/1991 | Laubscher |
| 7,288,664 B2 | 10/2007 | Kleiner |
| 7,714,160 B2 | 5/2010 | Sugise et al. |

FOREIGN PATENT DOCUMENTS

| CN | 1048098 A | | 12/1990 | |
| CN | 1772600 A | | 5/2006 | |
| CN | 101143821 A | | 3/2008 | |
| CN | 101492370 | * | 7/2009 | ............. C07C 69/36 |
| CN | 101492370 A | | 7/2009 | |
| CN | 101993366 A | * | 3/2011 | ............. C07C 67/36 |
| CN | 201770631 A | | 3/2011 | |
| SU | 1298188 A1 | | 3/1987 | |

OTHER PUBLICATIONS

Office Action dated Mar. 18, 2013, issued in corresponding Chinese Patent Application No. 201010200028.1. (5 pages).
International Search Report (PCT/ISA/210) issued on Sep. 15, 2011, by the Chinese Patent Office as the International Searching Authority for International Application No. PCT/CN2011/000965.
International Preliminary Report on Patentability (PCT/IPEA/409) issued on Sep. 5, 2012, by the Chinese Patent Office for International Application No. PCT/CN2011/000965.
Office Action issued on Feb. 26, 2014, by the Russian Patent Office in corresponding Russian Patent Application No. 2013100936 and an English translation of the Office Action. (7 pages).
Decision on Grant of Patent for Invention issued on Jun. 24, 2014, by the Russian Federation Patent Office in corresponding Russian Patent Application No. 2013100936, with an English translation (13 pages).

* cited by examiner

*Primary Examiner* — Brandon Fetterolf
*Assistant Examiner* — Janet L Coppins
(74) *Attorney, Agent, or Firm* — Buchanan Ingersoll & Rooney PC

(57) ABSTRACT

A process of producing oxalate by CO gas phase method includes the following steps: a) introducing nitrite salt, water and an inorganic acid first into a reactor I to produce a NO containing effluent I; and separating the resultant effluent to obtain the effluent II of NO; b) introducing the effluent II of NO, a $C_1$-$C_4$ alkanol and oxygen into a reactor II to be subjected to the reaction, and separating the resultant effluent to obtain the effluent IV of $C_1$-$C_4$ alkyl nitrites; c) introducing the effluent IV of $C_1$-$C_4$ alkyl nitrites and a CO gas stream into a coupling reactor where they are reacted to produce a NO containing effluent VI. The reactor I and/or the reactor II are preferably rotating supergravity reactors. Therefore, the process is applicable to the industrial production of oxalate by CO gas phase method.

10 Claims, No Drawings

PROCESS OF PRODUCING OXALATE BY CO GAS PHASE METHOD

TECHNICAL FIELD

The present invention relates to a process of producing oxalate by CO gas phase method, especially to a process of producing oxalate by CO gas phase method with respect to the production of oxalate by CO coupling, with the consumption of nitrogen oxides greatly reduced.

BACKGROUND ART

Oxalate is the important raw material in the organic chemical industry, which is used on a large scale for producing various dyes, medicines, important solvents, extracting agents and various intermediates in the industry of fine chemicals. Upon the advent of the $21^{st}$ century, as the environmentally friendly biodegradable engineering plastic monomer, oxalate is widely valued in the international world. Besides, the hydrolysis of oxalate at normal pressure can produce oxalic acid and the aminolysis at normal pressure can produce oxamide which is a high-quality and slowly-releasing fertilizer. Oxalate can also be used as solvents and for producing the intermediates of medicines and dyes etc., for example the various condensation reactions between oxalate and fatty acid esters, cyclohexyl acetyl benzene, amino alcohols and many heterocyclic compounds can be carried out. Oxalate can also be used for synthesizing thymine used as hormone in medicine. Besides, the hydrogenation of oxalate at low pressure can produce ethylene glycol which is a significant raw material in the chemical industry. However, currently, the production of ethylene glycol primarily relies on the petroleum route at high cost. China needs an enormous amount of imported ethylene glycol each year. In 2007, the import quantum is almost 4.8 million tons.

The traditional production method of oxalate is to utilize oxalic acid by the esterification thereof with alcohols. This producing technique is expensive in terms of costs, consumes great energy, results in a heavy pollution and an unreasonable use of raw materials. For many years, people are seeking for a low cost, environmentally friendly process route. In the sixties of last century, D. F. Fenton from Unocal Corp of USA found that CO, alcohol and oxygen can be used to directly synthesize dialkyl oxalate by the oxidative carbonylation reation. Since then, Ube Industries from Japan and American Atlantic Richfield Company (ARCO) successively carried out researches and developments in this field.

In terms of the developmental course, the processes of synthesizing oxalate by CO oxidative coupling method can be divided into two processes, namely the liquid phase method and the gas phase method. The conditions of synthesizing oxalate by CO liquid phase method are comparatively stringent as the reaction is carried out at high pressure and the liquid phase system thereby tends to corrode the equipment and the catalyst during the reaction tends to run off. The CO coupling gas phase method of producing oxalate is the most advantageous. Abroad, Ube Industries and Montedison from Italy successively carried out the researches on the gas phase method in 1978, wherein Ube Industries developed the technology of gas phase catalytic synthesis of oxalate at a reaction pressure of 0.5 Mpa and a temperature of 80° C.-150° C.

The reaction course of synthesizing oxalate is as follows:

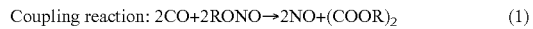

Coupling reaction: $2CO+2RONO \rightarrow 2NO+(COOR)_2$     (1)

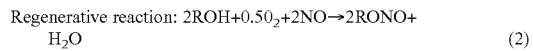

Regenerative reaction: $2ROH+0.5O_2+2NO \rightarrow 2RONO+ H_2O$     (2)

It is evident from the course above that theoretically, this system does not consume NO or RONO (alkyl nitrite), but actually, during the reaction of step (2); in addition to the production of RONO as the primary product, side reactions often occur, especially the production of dilute nitric acid as the by-product. This must consume more NO gas. Thus, NO must be incessantly supplemented to the reaction system so that the catalytic reaction of synthesizing oxalate can go on stably and continuously for a long time. Under usual situations, NO comes from the products of ammonia oxidation or the end gases of nitric acid. However, the products of ammonia oxidation or the end gases of nitric acid, besides NO or $NO_2$ as required, further comprise the gases like $N_2$, Ar, He etc. which are nonreactive and difficult to be condensed. If a large amount of the said gases enter the system of synthesizing oxalate, said gases will be very adverse to the catalytic reaction of synthesizing oxalate, or even stop the reaction. The successful reaction can only be guaranteed when these nonreactive gases are discharged from the reaction system. Nevertheless, when the gases like $N_2$, Ar, He etc. which are nonreactive and difficult to be condensed are discharged from the reaction system, the useful reactive substances in the synthetic reaction system such as NO and RONO will be also taken out at the same time. In that case, the raw materials are wasted and the environment is polluted. Thus, NO and RONO must be effectively recovered and the treatment of eliminating the environmental pollution must be carried out. It can thus be seen that the key points of increasing the low efficiency of utilizing nitrogen oxides or nitrous acid esters are that on the one hand, the occurrences of the side reactions (e.g. the reaction of generating nitric acid) during the reaction course (including the reaction of introducing nitrogen oxides or nitrous acid esters into the system and the normal cyclic reaction course) should be reduced, and meanwhile, the losses of the materials of nitrogen oxides or nitrous acid esters taken out by the incondensable gases while discharging should be reduced to the utmost extent.

The patent CN1048098A utilized the method of combining compression and condensation to accomplish this task, but the operation conditions required by the patent were comparatively stringent and the effects were poor. Patent CN200510107783.4 further improved CN1048098A and disclosed a new production method of synthesizing oxalate by using NO. Firstly, alcohols were primarily used to absorb a large amount of nitrous acid esters. Then, the method of combining compression and condensation was used to condense the small amount of alcohols and nitrous acid esters in the gas phase into liquids at a pressure of 0.1-10 MPa and a condensation temperature of −20° C.~100° C. The alcohols and the nitrous acid esters and the incondensable gases were separated, and then the recovered condensed liquids were recycled and the incondensable gases were discharged. Obviously, the method also suffers from the problem of the strict operation conditions and meanwhile the high costs of operation energy and the low utilization efficiency of nitrogen oxides or nitrous acid esters.

The supergravity technology is a new technology of enhancing the multiphase flow delivery and reaction course. Since the technology came out in the last century, it has been widely valued both domestically and abroad. Because it has the wide applicability and the advantages of small volume, light weight, low energy consumption, easy operation, easy maintenance, safety, reliability, flexibility and being more adaptive to environment etc. which the traditional instruments do not possess, the commercializing application of the supergravity technology in the industrial fields like environmental protection, the chemical industries of materials and biology is very encouraging. However, at present, the supergravity technology is primarily at the stage of the development of applications thereof. Moreover, the use of the supergravity rotating bed reactor in the production of $C_1$-$C_4$ alkyl nitrites and thereby the production of oxalate have not been reported yet.

CONTENTS OF THE INVENTION

The technical problems solved by the present invention are the low utilization efficiency and the low selectivity of nitrogen oxides or nitrous acid esters in the prior art, and provides a new process of producing oxalate by CO gas phase method, which has the advantages of the high utilization efficiency and the high selectivity of nitrogen oxides or nitrous acid esters.

For solving the technical problem above, the technical solution used in the present invention is as follows: A process of producing oxalate by CO gas phase method comprises the following steps:

a) Nitrite salt; water and inorganic acid first enter a reactor I to produce an NO containing effluent I; an effluent II of NO is then obtained by separating the effluent I;
b) the effluent II of NO and $C_1$-$C_4$ alkanol and oxygen enter a reactor II to be subjected to the oxidative esterification reaction to produce an effluent HI comprising $C_1$-$C_4$ alkyl nitrites which is then separated to give an effluent IV of $C_1$-$C_4$ alkyl nitrites;
c) the effluent IV of $C_1$-$C_4$ alkyl nitrites and a CO gas stream enter a coupling reactor where they are contacted with a Pd-containing catalyst and reacted to produce an effluent V of oxalate and an NO containing effluent VI;
d) optionally, the NO containing effluent VI is returned to step b) for being mixed with the effluent II of NO and then continuing to participate into the reaction.

In one preferred embodiment of the invention, the reactor I and/or the reactor II are rotating supergravity reactors. More preferably, the rotor of the rotating supergravity reactor of the reactor I has a rotational speed of 300-6000 rpm, preferably 500-4000 rpm, and/or the rotor of the rotating supergravity reactor of the reactor II has a rotational speed of 300-6000 rpm, preferably 500-4000 rpm.

In another preferred embodiment of the invention, the Pd-containing catalyst contains Pd in an amount of 0.01-1 wt. %, preferably 0.01-0.8 wt %, more preferably 0.03-0.7 wt. % based on the weight of the catalyst support.

In another preferred embodiment of the invention, for the reactor I, the molar ratio of the water to nitrite salt is 1~20:1, preferably 1.2~10:1; the molar ratio of inorganic acid to nitrite salt is from 0.2~5:1, preferably 0.4~3 1; the reaction temperature is 0~100° C., preferably 10~70° C.; the reaction pressure is −0.08~1.0 MPa, preferably −0.05~1.0 MPa; the reaction contacting time is 0.01~50 s, preferably 0.02~30 s. For the reactor II, the reaction temperature is 20~100° C., preferably 25~70° C.; the reaction pressure is −0.08~2.0 MPa, preferably −0.05~1.0 MPa; the reaction contacting time is 0.01~60 s, preferably 0.02~40 s; the molar ratio of NO in the NO containing effluent II and the NO containing effluent VI, $C_1$-$C_4$ alkanol and oxygen is 1:1~50:0.01~0.25, preferably 1:1~20:0.1~0.25.

In another preferred embodiment of the invention, the coupling reactor has a reaction temperature of 80-160° C., preferably 90-150° C.; a reaction contacting time of 0.1-100 s, preferably 0.5-50 s; a reaction pressure of −0.05~2.0 MPa, preferably 0.01~1.0 MPa; a molar ratio of the CO gas to the effluent IV of C1-C4 alkyl nitrites of from 1.1~15:1, preferably from 1.1~10:1.

In another preferred embodiment of the invention, the nitrite salts are nitrite salts of alkali metals or alkali earth metals, preferably sodium . nitrite, potassium nitrite and magnesium nitrite.

In another preferred embodiment of the invention, the inorganic acid is sulfuric acid and nitric acid.

In another preferred embodiment of the invention, $C_1$-$C_4$ alkanol is selected from the group consisting of methanol, ethanol, propanol and butanol, preferably methanol and ethanol.

It is well-known that during the two-step reaction process of preparing ethylene glycol by a synthesizing gas, the selection of the CO coupling route of producing oxalate is very important. In view of the practical industrial applications, it is generally, thought that the technical route of firstly producing an oxalate by CO coupling, and then hydrogenating the oxalate to produce ethylene glycol is the most feasible. However, the CO coupling reaction course needs to consume NO. Therefore, during supplementing the NO raw material to the process of producing the oxalate by CO coupling, under general situations, alcohol, oxygen and NO are used to be subjected to oxidative esterification, and then the nonreactive gases are exhausted by the method of combining compression, condensation and alcohol absorption, and then the nitrite resulting from NO reaction is introduced into the system and reacted. However, the confronted problems are the complex procedures, the high energy consumption and the low utilization efficiency of nitride oxides of the process. In the present invention, the way of reacting nitrite salts with inorganic acids to directly produce NO and then directly supplementing NO to the coupling system is used to replace the common way of supplementing NO via ammonia oxidation. The technical solution has the following technical advantages:

(1) mild reaction conditions, high reaction efficiency, high purity of NO;
(2) no inert gas during the reaction process, no loss of nitride oxides caused by the discharging process of the system inert gas resulting from the accumulation of the inert gas during the supplement process of the system;
(3) low costs; the salts of the inorganic acids converted from the nitrite salts as the reaction raw materials being also useful raw materials of the chemical industry.

Besides, it is well-known that every matter on the Earth is attracted by the Earth because of gravity. The supergravity field is an environment which is much more intense than the gravity field of the Earth. The force exerted on a substance by the supergravity field is called supergravity, and the practical technology developed by making use of the scientific principle of supergravity is called as the supergravity technology. In the supergravity environment which is hundreds or even thousands of times greater than the gravity field of the Earth, the enormous shearing force tears liquid into from microscale to nanoscale liquid films, liquid filaments, liquid drops, and produces great and rapidly updated phase interface, and thereby dramatically increase the contact specific surface area so that the interphase mass transfer rate is increased by 1-3 orders of magnitude as compared with the rate in the traditional towers or reactors and the processes of micromixing, mass transfer and heat transfer are also greatly enhanced, leading to an increase of 1-2 orders of magnitude of the production efficiency of unit equipment volume.

In the preferred technical solution of the present invention, while the supergravity reaction technology is introduced into the supplementing reaction system of NO and/or the oxidative esterification process of NO and oxygen and alcohols during the coupling reaction, the further enhancement of the mass transfer and heat transfer processes can effectively promote the primary reaction and inhibit the occurrences of side reactions, thereby dramatically improving the selectivity of nitrous acid esters. Additionally, for the reactor I, with view to the solubilities of the nitrite salts as the raw materials and the salts of inorganic acids as the products in the reactants, the present invention also uses water as the diluent for ensuring the uniformly mixing of the raw materials on the one hand, and simultaneously preventing the salts produced in the reactions from precipitating as crystals which clog the reaction system so that the reaction process remains stable and steady.

For example, the preferred technical solution of the present invention is: nitrite salt, water and inorganic acid first enter a reactor I to produce an NO containing effluent I; an effluent II of NO is then obtained by separating the effluent I; the effluent II of NO and $C_1$-$C_4$ alkanol and oxygen enter a reactor II to be subjected to the oxidative esterification reaction to produce an effluent III comprising $C_1$-$C_4$ alkyl nitrites which is then separated to give an effluent IV of $C_1$-$C_4$ alkyl nitrites; and the effluent IV of $C_1$-$C_4$ alkyl nitrites and a CO gas stream enter a coupling reactor where they are contacted with a Pd-containing catalyst and reacted to produce an effluent V of oxalate and an NO containing effluent VI; the NO containing effluent VI is returned to step b) for being mixed with the effluent II of NO and then continuing to participate into the reaction; here, the reactor I and/or the reactor II are preferably rotating supergravity reactors; Pd-containing catalyst contains Pd in an amount of 0.01-1 wt. % based on the weight of the catalyst support. For the reactor I, the molar ratio of the water to nitrite salt is 1~20:1; the molar ratio of inorganic acid to nitrite salt is 0.2~5:1; the reaction temperature is 0~100° C.; the reaction pressure is −0.08~1.0 MPa; the reaction contacting time is 0.01~50 s. For the reactor II, the reaction temperature is 20~100° C.; the reaction pressure is −0.08~2.0 MPa; the reaction contacting time is 0.01~60 s; the molar ratio of NO in the NO containing effluent II and the NO containing effluent VI, C1-C4 alkanol and oxygen is 1:1~50: 0.01~0.25; the coupling reactor has a reaction temperature of 80-160° C.; a reaction contacting time is 0.1-100 s; a reaction pressure is −0.05-2.0 MPa; a molar ratio of the CO gas to the effluent IV of C1-C4 alkyl nitrites of from 1.1~15:1. If the reactor I and/or the reactor II are rotating supergravity reactors, the rotor of the rotating supergravity reactor of the reactor I and/or the reactor II has a rotational speed of 300-6000 rpm.

According to the method of the present invention, the selectivity of the NO is greater than or equal to 98%, preferably greater than or equal to 99%. Thus, excellent technical effects are obtained.

The present invention is further demonstrated via the following examples, but not limited to the examples.

EXAMPLES

Example 1

Sodium nitrite, water and inorganic acid first enter a reactor I to produce an NO containing effluent I; an effluent II of NO is then obtained by separating the effluent I; the effluent II of NO and methanol and oxygen enter a reactor. II to be subjected to the oxidative esterification reaction to produce an effluent III comprising methyl nitrite; said effluent III is separated to obtain the effluent IV of methyl nitrite; said effluent IV of methyl nitrite and a CO gas stream enter a coupling reactor where they are contacted with a Pd-containing catalyst and reacted to produce an effluent V of oxalate and an NO containing effluent VI; the NO containing effluent VI is returned to an entrance of the reactor II for being mixed with the effluent II of NO and then continuing to participate into the reaction; here, both the reactor I and the reactor II are rotating supergravity reactors; Pd-containing catalyst contains Pd in an amount of 0.5 wt. % based on the weight of the catalyst support. For the reactor I, the molar ratio of water to sodium nitrite is 2:1; the molar ratio of sulphuric acid to sodium nitrite is 0.5:1; the reaction temperature is 10 C; the reaction pressure is −0.05 MPa; the reaction contacting time is 0.05 s. For the reactor II, the reaction temperature is 30° C.; the reaction pressure is −0.05 MPa; the reaction contacting time is 0.02 s; the molar ratio of NO in the NO effluent II and the NO containing effluent VI, methanol and oxygen is 1:2: 0.2; the coupling reactor has a reaction temperature 100° C.; a reaction contacting time is 2 s; a reaction pressure is −0.05 MPa; a molar ratio of CO in the CO gas stream to methyl nitrite is 1.5:1; the rotor of the rotating supergravity reactor of the reactor I and the reactor II has a rotational speed of 600 rpm. The results are: a selectivity of NO of the reactor I of 99.99%, the selectivity of the nitrous acid ester of the reactor II of 98.9%, a space time yield of dimethyl oxalate of the coupling reactor of 860 g/(h.L); and a selectivity of dimethyl oxalate of 98.9%.

Example 2

Potassium nitrite, water and sulphuric acid first enter a reactor I to produce an NO containing effluent I; an effluent II of NO is then obtained by separating the effluent I; the effluent II of NO and methanol and oxygen enter a reactor II to be subjected to the oxidative esterification reaction to produce an effluent III comprising methyl nitrite; said effluent III is separated to obtain the effluent IV of methyl nitrite; said effluent IV of methyl. nitrite and a CO gas stream enter a coupling reactor where they are contacted with a Pd-containing catalyst and reacted to produce an effluent V of oxalate and an NO containing effluent VI; the NO containing effluent VI is returned to an entrance of the reactor II for being mixed with the effluent II of NO and then continuing to participate into the reaction; here, both the reactor I and the reactor II are rotating supergravity reactors; Pd-containing catalyst contains Pd in an amount of 0.3 wt. % based on the weight of the catalyst support. For the reactor I, the molar ratio of water to potassium nitrite is 3:1; the molar ratio of sulphuric acid to potassium nitrite is 0.6:1; the reaction temperature is 20° C.; the reaction pressure is 0.05 MPa; the reaction contacting time is 0.08 s. For the reactor II, the reaction temperature is 30° C.; the reaction pressure is 0.05 MPa; the reaction contacting time is 0.05 s; the molar ratio of NO in the NO containing effluent II and the NO containing effluent VI, methanol and oxygen is 1:2:0.2; the coupling reactor has a reaction temperature 120° C.; a reaction contacting time is 1 s; a reaction pressure is −0.05 MPa; a molar ratio of CO in the CO gas stream to methyl nitrite is 1.3:1; the rotor of the rotating supergravity reactor of the reactor I and the reactor II has a rotational speed of 700 rpm. The results are: a selectivity of the NO of the reactor I of 99.98%, the selectivity of the nitrous acid ester of the reactor II of 99.3%, a space time yield of dimethyl oxalate of the coupling reactor of 880 g/(h.L); and a selectivity of dimethyl oxalate of 99.2%.

Example 3

Magnesium nitrite, water and nitric acid first enter a reactor I to produce an NO containing effluent I; an effluent II of NO is then obtained by separating the effluent I; the effluent II of NO and methanol and oxygen enter a reactor II to be subjected to the oxidative esterification reaction to produce an effluent III comprising methyl nitrite; said effluent III is separated to obtain the effluent IV of methyl nitrite; said effluent IV of methyl nitrite and a CO gas stream enter a coupling reactor where they are contacted with a Pd-containing catalyst and reacted to produce an effluent V of oxalate and an NO containing effluent VI; the NO containing effluent VI is returned to an entrance of the reactor II for being mixed with the effluent II of NO and then continuing to participate into the reaction; here, both the reactor I and the reactor II are rotating supergravity reactors; Pd-containing catalyst contains Pd in an amount of 0.4 wt. % based on the weight of the catalyst support. For the reactor I, the molar ratio of water to magnesium nitrite is 3:1; the molar ratio of nitric acid to magnesium nitrite is 2:1; the reaction temperature is 20° C.; the reaction pressure is 0.01 MPa; the reaction contacting time is 0.1 s. For the reactor II, the reaction temperature is 40° C.; the reaction pressure is 0.02 MPa; the reaction contacting time is 0.2 s; the molar ratio of NO in the NO effluent II and the NO containing effluent VI, methanol and oxygen is 1:3:0.2; the coupling reactor has a reaction temperature 130 ° C.; a reaction contacting time is 2 s; a reaction pressure is −0.02 MPa; a molar ratio of CO in the CO gas stream to methyl nitrite is 1.2:1; the rotor of the rotating supergravity reactor of the reactor I and the reactor II has a rotational speed of 800 rpm. The results are: a selectivity of the NO of the reactor I of 99.99%, the selectivity of the nitrous acid ester of the reactor II of 99.5%, a space time yield of dimethyl oxalate of the coupling reactor of 890 g/(h.L); and a selectivity of dimethyl oxalate of 99.6%.

Example 4

Potassium nitrite, water and nitric acid first enter a reactor I to produce an NO containing effluent I; an effluent II of NO is then obtained by separating the effluent I; the effluent II of NO and methanol and oxygen enter a reactor II to be subjected to the oxidative esterification reaction to produce an effluent III comprising methyl nitrite; said effluent III is separated to obtain the effluent IV of methyl nitrite; said effluent IV of methyl nitrite and a CO gas stream enter a coupling reactor where they are contacted with a Pd-containing catalyst and reacted to produce an effluent V of oxalate and an NO containing effluent VI; the NO containing effluent VI is returned to an entrance of the reactor II for being mixed with the effluent II of NO and then continuing to participate into the reaction; here, both the reactor I and the reactor II are rotating supergravity reactors; Pd-containing catalyst contains Pd in an amount of 0.4 wt. % based on the weight of the catalyst support. For the reactor I, the molar ratio of water to potassium nitrite is 3:1; the molar ratio of nitric acid to potassium nitrite is 2:1; the reaction temperature is 20° C.; the reaction pressure is 0.01 MPa; the reaction contacting time is 0.1 s. For the reactor II, the reaction temperature is 40° C.; the reaction pressure is 0.02 MPa; the reaction contacting time is 0.2 s; the molar ratio of NO in the NO containing effluent II and the NO containing effluent VI, methanol and oxygen is 1:5:0.2; the coupling reactor has a reaction temperature 140° C.; a reaction contacting time is 2 s; a reaction pressure is −0.02 MPa; a molar ratio of CO in the CO gas stream to methyl nitrite is 1.2:1; the reactor I is an agitation reactor which has a rotational speed of 100 rpm. The rotor of the rotating supergravity reactor of the reactor II has a rotational speed of 800 rpm, The results are: a selectivity of the NO of the reactor I of 99.50%, the selectivity of the nitrous acid ester of the reactor II of 99.3%, a space time yield of dimethyl oxalate of the coupling reactor of 900 g/(h.L);, and a selectivity of dimethyl oxalate of 99.1%.

Example 5

The procedure is carried out according to Example 1, except that the Pd-containing catalyst comprises Pd in an amount of 0.8 wt. % based on the weight of the catalyst support. For the reactor I, the molar ratio of the water to sodium nitrite is 15:1. The molar ratio of sulphuric acid to sodium nitrite is 3:1. The reaction temperature is 20° C. The reaction pressure is −0.02 MPa. The reaction contacting time is 0.1 s. The reaction temperature of the reactor II is 50° C. The reaction pressure is '10.02 MPa. The reaction contacting time is 0.08 s. The molar ratio of NO in the NO containing effluent II and the NO containing effluent VI, methanol and oxygen is 1:5:0.22. The coupling reactor has a reaction temperature 120° C. A reaction contacting time is 10 s. A reaction pressure is −0.01 MPa. A molar ratio of CO gas to methyl nitrite is 2:1. The rotor of the rotating supergravity reactor of the reactor I and the reactor II has a rotational speed of 1000 rpm. The results are: a selectivity of the NO of the reactor I of 100%, a selectivity of the nitrous acid ester of the reactor II of 99.2%, a space time yield of dimethyl oxalate of the coupling reactor of 890 g/(h.L); and a selectivity of dimethyl oxalate of 99.1%.

Example 6

The procedure is carried out according to Example 1, except that the Pd-containing catalyst comprises Pd in an amount of 0.8 wt. % based on the weight of the catalyst support. For the reactor I, the molar ratio of water to sodium nitrite is 2:1. The molar ratio of sulphuric acid to sodium nitrite is 0.3:1. The reaction temperature is 30° C. The reaction pressure is −0.05 MPa. The reaction contacting time is 1 s. For the reactor II, the reaction temperature is 80 ° C. The reaction pressure is 0.2 MPa. The reaction contacting time is 2 s. The molar ratio of NO in the NO containing effluent II and the NO containing effluent VI, methanol and oxygen is 1:10:0.15. The coupling reactor has a reaction temperature 140° C. A reaction contacting time is 60 s. A reaction pressure is 1.0 MPa. A molar ratio of CO gas to methyl nitrite is 3:1. The rotor of the rotating supergravity reactor of the reactor I and the reactor H has a rotational speed of 2000 rpm. The results are: a selectivity of the NO of the reactor I of 99.8%, a selectivity of the nitrous acid ester of the reactor II of 99.3%, a space time yield of dimethyl oxalate of the coupling reactor of 910 g/(h.L); and a selectivity of dimethyl oxalate of 99.3%.

Example 7

The procedure is carried out according to Example 1, except that the Pd-containing catalyst comprises Pd in an amount of 0.2 wt. % based on the weight of the catalyst support. For the reactor I, the molar ratio of water to sodium nitrite is 15:1. The molar ratio of nitric acid to sodium nitrite is 5:1. The reaction temperature is 80° C. The reaction pressure is 0.8 MPa. The reaction contacting time is 1 s. For the reactor II, the reaction temperature is 40° C. The reaction pressure is 0.8 MPa. The reaction contacting time is 40 s. The molar ratio of NO in the NO containing effluent II and the NO containing effluent VI, alcohol and oxygen is 1:20:0.11. The coupling reactor has a reaction temperature 160° C. A reaction contacting time is 80 s. A reaction pressure is 0.5 MPa. A molar ratio of CO gas to ethyl nitrite is 6:1. The rotor of the rotating supergravity reactor of the reactor I and the reactor II has a rotational speed of 3000 rpm. The results are: a selectivity of the NO of the reactor I of 100%, a selectivity of the nitrous acid ester of the reactor II of 99.5%, a space time yield of dimethyl oxalate of the coupling reactor of 1100 g/(h.L); and a selectivity of dimethyl oxalate of 99.0%.

Example 8

The procedure is carried out according to Example 1, except that the Pd-containing catalyst comprises Pd in an amount of 0.3 wt. % based on the weight of the catalyst support. For the reactor I, the molar ratio of water to sodium nitrite is 3:1. The molar ratio of sulphuric acid to sodium nitrite is 4:1. The reaction temperature is 40° C. The reaction pressure is 0.2 MPa. The reaction contacting time is 40 s. For the reactor II, the reaction temperature is 50° C. The reaction pressure is 0.2 MPa. The reaction contacting time is 10 s. The molar ratio of NO in the NO containing effluent II and the NO containing effluent VI, propanol and oxygen is 1:45:0.05. The coupling reactor has a reaction temperature 100° C. A reaction contacting time is 40 s. A reaction pressure is 0.1 MPa. A molar ratio of CO gas to propyl nitrite is 1.5:1. The rotor of the rotating supergravity reactor of the reactor I and the reactor II has a rotational speed of 2000 rpm. The results are: a selectivity of the NO of the reactor I of 100%, a selectivity of the nitrous acid ester of the reactor II of 98.9%, a space time yield of dimethyl oxalate of the coupling reactor of 880 g/(h.L); and a selectivity of dimethyl oxalate of 99.4%.

Example 9

The procedure is carried out according to Example 1, except that the Pd-containing catalyst comprises Pd in an amount of 0.6 wt. % based on the weight of the catalyst support. For the reactor I, the molar ratio of water to potassium nitrite is 5:1. The molar ratio of sulphuric acid to potassium nitrite is 2.3:1, The reaction temperature is 40 ° C. The reaction pressure is −0.01 MPa. The reaction contacting time is 0.5 s. For the reactor II, the reaction temperature is 40° C. The reaction pressure is −0.02 MPa. The reaction contacting time is 0:8 s. The molar ratio of NO in the NO containing effluent II and the NO containing effluent VI, methanol and oxygen is 1:10:0.08. The coupling reactor has a reaction temperature 130° C. A reaction contacting time is 5 s. A reaction pressure is 0.01 MPa. A molar ratio of CO gas to methyl nitrite is 1:3:1. The rotor of the rotating supergravity reactor of the reactor I has a rotational speed of 1000 rpm. The rotor of the rotating supergravity reactor of the reactor II has a rotational speed of 2000 rpm. The results are: a selectivity of the NO of the reactor I of 100%, a selectivity of the nitrous acid ester of the reactor II of 99.5%, a space time yield of dimethyl oxalate of the coupling reactor of 1008 g/(h.L); and a selectivity of dimethyl oxalate of 99.5%.

Example 10

The procedure is carried out according to Example 1, except that the Pd-containing catalyst comprises, Pd in an amount of 0.7 wt. % based on the weight of the catalyst support. For the reactor I, the molar ratio of water to sodium nitrite is 4:1. The molar ratio of sulphuric acid to sodium nitrite is 2.1:1. The reaction temperature is 30 ° C. . The reaction pressure is 0.1 MPa. The reaction contacting time is 0.2 s. For the reactor II, the reaction temperature is 50° C., The reaction pressure is 0.2 MPa. The reaction contacting time is 0.3 s. The molar ratio of NO in the NO containing effluent II and the NO containing effluent VI, methanol and oxygen is 1:3:0.24, The coupling reactor has a reaction temperature 90° C. A reaction contacting time is 20 s. A reaction pressure is 0.08 MPa. A molar ratio of CO gas to methyl nitrite is 1.2:1. The rotor of the rotating supergravity reactor of the reactor I has a rotational speed of 1500 rpm. The rotor of the rotating supergravity reactor of the reactor II has a rotational speed of 3000 rpm. The results are: a selectivity of the NO of the reactor I of 100%, a selectivity of the nitrous acid ester of the reactor II of 99.6%, a space time yield of dimethyl oxalate of the coupling reactor of 800 g/(h.L); and a selectivity of dimethyl oxalate of 99.6%.

Example 11

There are the same catalyst, conditions and reactions materials as those in example 2, except that the fixed-bed reactors are used as the reactor I and the reactor II. The results are: a selectivity of the NO of the reactor I of 99.1%, a selectivity of the nitrous acid ester of the reactor II of 95.5%, a space time yield of dimethyl oxalate of the coupling reactor of 860 g/(h.L); and a selectivity of dimethyl oxalate of 98.6%.

Example 12

There are the same catalyst, conditions and reactions materials as those in example 9, except that the agitation reactor is used as the reactor I having a rotational speed of 150 rpm; the reactor II is a fixed-bed reactor. The results are: a selectivity of the NO of the reactor I of 98%, a selectivity of the nitrous acid ester of the reactor II of 92.5%, a space time yield of dimethyl oxalate of the coupling reactor of 960 g/(h.L); and a selectivity of dimethyl oxalate of 98.8%.

Comparative Example 1

There are the same catalyst, conditions and reaction materials as those in Example 2, except that the reactor I and the reactor II are replaced with an ammonia reaction furnace (the reactor I) in Patent CN200510107783.4 to provide NO and with an esterification reaction tower (the reactor II) to produce methyl nitrite. The results are: a selectivity of NO of the reactor I of 85%, a selectivity of the nitrous acid ester of the reactor II of 90.5%, a space time yield of dimethyl oxalate of the coupling reactor of 840 g/(h.L); and a selectivity of dimethyl oxalate of 97.1%.

According to the comparison results above, it can be obviously seen that the method of the present invention achieves notable technical effects.

The invention claimed is:
1. A process of producing oxalate by CO gas phase method comprising:
  a) introducing sodium nitrite, water and sulphuric acid first into a rotating supergravity reactor I to produce a NO containing effluent I which is then separated to give an effluent II of NO;
  b) introducing the effluent II of NO, a $C_1$-$C_4$ alkanol and oxygen into a rotating supergravity reactor II where the effluent II of NO, $C_1$-$C_4$ alkanol and oxygen are subjected to an oxidative esterification reaction to produce an effluent III comprising $C_1$-$C_4$ alkyl nitrites which is then separated to give an effluent IV of $C_1$-$C_4$ alkyl nitrites;
  c) introducing the effluent IV of $C_1$-$C_4$ alkyl nitrites and a CO gas stream into a coupling reactor where the effluent IV of $C_1$-$C_4$ alkyl nitrites and CO gas stream are con- tacted with a Pd-containing catalyst and reacted to produce an effluent V of oxalate and a NO containing effluent VI; and d) subjecting the NO containing effluent VI to step b) for being mixed with the effluent II of NO and then continuing to participate into the reaction, wherein the Pd-containing catalyst comprises Pd in an amount of 0.01~1 wt. % based on a weight of a catalyst support.

2. The process of producing oxalate by CO gas phase method according to claim 1, wherein the rotating supergravity reactor I comprises a rotator having a rotational speed of 300~6000 rpm, and/or the rotating supergravity reactor II comprises a rotator having a rotational speed of 300~6000 rpm.

3. The process of producing oxalate by CO gas phase method according to claim 1, wherein the Pd-containing catalyst comprises Pd in an amount of 0.01~0.8 wt. % based on the weight of the catalyst support.

4. The process of producing oxalate by CO gas phase method according to claim 1, wherein for the rotating supergravity reactor I, a molar ratio of water to sodium nitrite is 1~20:1; a molar ratio of sulphuric acid to sodium nitrite is 0.2~5:1; a reaction temperature is 0~100 ° C.; a reaction pressure is −0.08~1.0 MPa; and/or a reaction contacting time is 0.01~50 s; and/or for the rotating supergravity reactor II, a reaction temperature is 20~100 ° C.; a reaction pressure is −0.08~2.0 MPa; a reaction contacting time is 0.01~60 s; and/or a molar ratio of NO containing in the NO effluent II and the NO containing effluent VI, the $C_1$-$C_4$ alkanol and oxygen is 1: 1~50:0.01~0.25.

5. The process of producing oxalate by CO gas phase method according to claim 1, wherein a reaction temperature of the coupling reactor is 80~160 ° C.; a reaction contacting time is 0.1~100 s; a reaction pressure is −0.05~2.0 MPa; and/or a molar ratio of CO gas to the effluent IV of $C_1$-$C_4$ alkyl nitrites is 1.1~15:1.

6. The process of producing oxalate by CO gas phase method according to claim 1, wherein the $C_1$-$C_4$ alkanol is selected from the group consisting of methanol, ethanol, propanol and butanol.

7. The process of producing oxalate by CO gas phase method according to claim 1, wherein the rotating supergravity reactor I comprises a rotator having a rotational speed of 500~4000 rpm, and/or the rotating supergravity reactor II comprises a rotator having a rotational speed of 500~4000 rpm.

8. The process of producing oxalate by CO gas phase method according to claim 1, wherein for the rotating supergravity reactor I, a molar ratio of water to sodium nitrite is 1.2~10:1; a molar ratio of sulphuric acid to sodium nitrite is 0.4~3:1; a reaction temperature is 10~70 ° C.; a reaction pressure is −0.05~1.0 MPa; and/or a reaction contacting time is 0.02~30 s; and/or for the rotating supergravity reactor II, a reaction temperature is 25~70 ° C.; a reaction pressure is −0.05~1.0 MPa; a reaction contacting time is 0.02~40 s; and/or a molar ratio of NO containing in the NO effluent II and the NO containing effluent VI, the $C_1$-$C_4$ alkanol and oxygen is 1:1~20:0.1~0.25.

9. The process of producing oxalate by CO gas phase method according to claim 1, wherein a reaction temperature of the coupling reactor is 90~150 ° C.; a reaction contacting time is 0.5~50 s; a reaction pressure is 0.01~1.0MPa; and/or a molar ratio of CO gas to the effluent IV of $C_1$-$C_4$ alkyl nitrites is 1.1~10:1.

10. The process of producing oxalate by CO gas phase method according to claim 1, wherein the $C_1$-$C_4$ alkanol is methanol or ethanol.

* * * * *